United States Patent [19]

Lew et al.

[11] Patent Number: 5,167,962
[45] Date of Patent: Dec. 1, 1992

[54] FILAMENT SYSTEM FOR DELIVERING A MEDICAMENT AND METHOD

[75] Inventors: Chel W. Lew; Jack D. Trevino, both of San Antonio, Tex.

[73] Assignee: Southwest Research Institute, San Antonio, Tex.

[21] Appl. No.: 744,636

[22] Filed: Aug. 8, 1991

Related U.S. Application Data

[63] Continuation of Ser. No. 528,131, May 23, 1990, abandoned.

[51] Int. Cl.⁵ .............................................. A61F 2/00
[52] U.S. Cl. ..................................... 424/426; 424/423; 424/424; 424/425; 424/438; 424/451
[58] Field of Search ............... 424/438, 426, 423, 424, 424/425, 451

[56] References Cited

U.S. PATENT DOCUMENTS

| | | | |
|---|---|---|---|
| 3,625,214 | 12/1971 | Higuchi | 128/260 |
| 3,786,813 | 1/1974 | Michaels | 128/260 |
| 3,844,285 | 10/1974 | Laby | 128/260 |
| 3,995,632 | 12/1976 | Nakano et al. | 128/260 |
| 4,111,202 | 9/1978 | Theeuwes | 128/260 |
| 4,177,256 | 12/1979 | Michaels et al. | 424/22 |
| 4,217,894 | 8/1980 | Franetzki | 128/213 R |
| 4,235,236 | 11/1980 | Theeuwes | 128/260 |
| 4,292,299 | 9/1981 | Suzuki et al. | 128/156 X |
| 4,309,996 | 1/1982 | Theeuwes | 128/260 |
| 4,367,741 | 1/1983 | Michaels | 128/260 |
| 4,425,117 | 1/1984 | Hugemann et al. | 604/93 |
| 4,439,197 | 3/1984 | Honda et al. | 604/891 |
| 4,455,144 | 6/1984 | Michaels | 604/892 |
| 4,507,115 | 3/1985 | Kambara et al. | 604/135 |
| 4,564,363 | 1/1986 | Bagnall et al. | 604/893 |
| 4,578,075 | 3/1986 | Urquhart et al. | 604/892 |
| 4,623,345 | 11/1986 | Laby | 604/892 |
| 4,627,851 | 12/1986 | Wong et al. | 604/892 |
| 4,642,230 | 2/1987 | Whitehead et al. | 424/15 |
| 4,758,436 | 7/1988 | Caldwell | 424/451 |
| 4,767,627 | 8/1988 | Caldwell | 424/426 |
| 4,878,905 | 11/1989 | Blass | 604/14 |
| 5,062,829 | 11/1991 | Pryor | 604/57 |

FOREIGN PATENT DOCUMENTS 8533008449 8/1985 European Pat. Off.

Primary Examiner—Thurman K. Page
Assistant Examiner—D. Gabrielle Phelan
Attorney, Agent, or Firm—Vaden, Eickenroht, Thompson, Boulware & Feather

[57] ABSTRACT

A filament system for delivery of a medicament in the intestine comprised of a material having the medicament contained therein which is coiled for ease in ingestion and to prevent uncoiling until the filament reaches the intestine. Once the coiled filament reaches the intestine and uncoils, the medicament is released therefrom. The filament is preferably comprised of a material which is water insoluble, semipermeable, enteric, or bioerodible to facilitate release of the medicament, and is provided with or comprised of a bioadhesive for retarding the passage of the filament through the intestine once uncoiled, with the result that therapeutically effective dosage levels are sustained for relatively long periods of time.

19 Claims, 1 Drawing Sheet

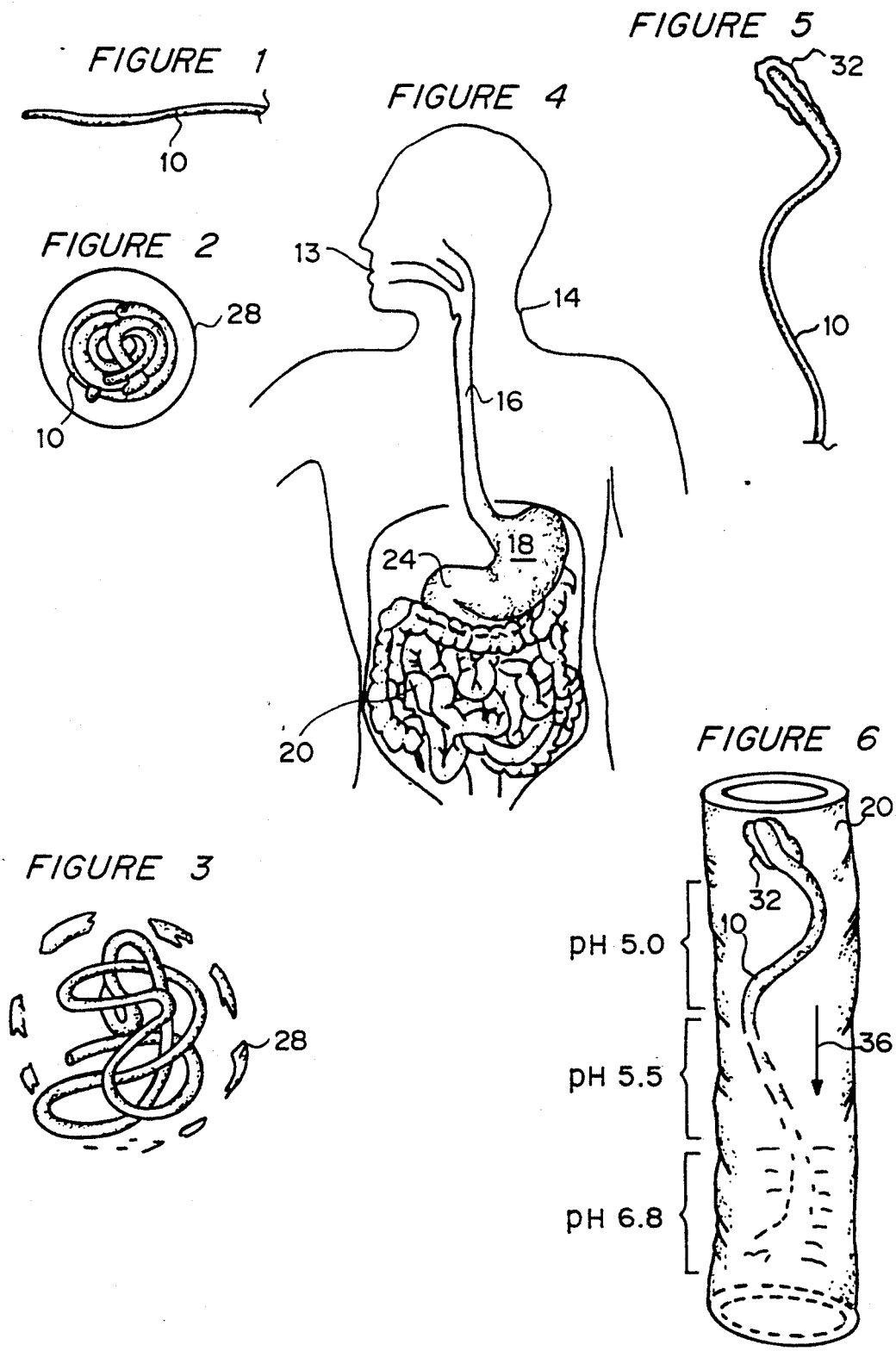

FILAMENT SYSTEM FOR DELIVERING A MEDICAMENT AND METHOD

This application is a continuation of application Ser. No. 528,131, filed on May 23, 1990, now abandoned.

BACKGROUND OF THE INVENTION

The present invention relates to the delivery of a medicament to the intestine. More particularly, the present invention relates to a system and method for delivering a medicament to the intestine by ingestion which is capable of delivering that medicament to the patient or animal for an extended period of time.

There have been a number of attempts to provide a system for delivering a medicament to the intestine which involve the oral ingestion of the medicament. The many benefits of such a system are summarized, for instance, in U.S. Pat. Nos. 3,901,232, 4,627,851, and 4,642,230, all of which are hereby incorporated herein in in their entirety by this specific reference thereto. These same references characterize many of the disadvantages of prior attempts to provide such systems, and the following brief summary of the pharmacokinetics of certain such systems and their disadvantages will suffice to provide an illustration of the motivation for the present invention.

Although the primary function of the small intestine is absorption, making that organ an ideal candidate for administration of a medicament or therapeutic agent, a number of factors combine to limit the use of that mode of delivery. For instance, the pH of the duodenal portion of the small intestine is about 4 to 5, but pH becomes more alkaline progressively farther along the length of the intestine, and the effect of pH on the bioavailability of many medicaments is well documented. The flora of the entire gastrointestinal tract may inactivate certain medicaments or otherwise reduce their absorption or bioavailability, and the digestive enzymes produced in the intestinal mucosa have the same effect on certain medicaments. Further, although passage through the small intestine is slow compared, for instance, to passage through the oral cavity or stomach, an orally ingested medicament does pass through, and eventually out of, the intestine, making administration of the medicament over a sustained period of time problematical.

It is these problems, particularly the latter, with which the present invention is concerned. Several prior art patents describe delivery systems which purport to address the problem of passage through the gastrointestinal tract and administration of a medicament over extended periods, but those references appear to do so in less then satisfactory fashion. For instance, U.S. Pat. Nos. 3,844,285 and 4,623,345 describe devices enclosing a medicament which, after ingestion, open to release the medicament in the gastrointestinal tract, the open container acting to retain the device in the gastrointestinal tract by physical engagement of the mucosa. Such devices remain in the gastrointestinal tract even after all the medicament has been released because of that engagement. As described in the above-incorporated U.S. Pat. No. 4,642,230, it is also known to use weights in a device in which the medicament is contained to retain the device within the gastrointestinal tract. However, the weight is generally a heavy metal and, even if coated to prevent oxidation of the metal, sooner or later, the ingestion of heavy metals will have deleterious effects. Neither such consequence is generally considered acceptable in the case of human patients.

Another problem relating to passage of the medicament through the intestine is that it is often necessary to coat the medicament for passage through the stomach. Such "enteric" coatings are of particular use in the case of those medicaments which are destroyed or inactivated by the acidic contents of the stomach or which cause gastric irritation. However, many enteric-coated medicaments resist dissolution in the intestine as well as the stomach such that comparatively little of the medicament may be absorbed before the coated medicament is passed. Other problems with such medicaments are characterized in L. Z. Benet and L. B. Sheiner, "Pharmacokinetics: The Dynamics of Drug Absorption, Distribution, and Elimination," in A. G. Gilman, et al. (Eds.), Goodman & Gilman's The Pharmacological Basis of Therapeutics (7th Ed.), New York: MacMillan Publishing Co., pp. 3–34 (1985), hereby incorporated in its entirety by this specific reference thereto.

It is, therefore, an object of the present invention to provide an improved system and method for delivery of a medicament in the intestine which overcomes the above-described disadvantages and limitations of prior known systems.

It is a particular object of the present invention to provide a filament system and method for delivery of a medicament in the intestine over an extended period of time.

It is another object of the present invention to provide a filament system and method for delivery of a medicament in the intestine for both topical and systemic therapy.

It is another object of the present invention to provide a filament system and method for delivery of a medicament in the intestine which does not release the medicament in the gastrointestinal tract until the system reaches the intestine.

It is another object of the present invention to provide a filament system and method for delivery of a medicament to a specific location in the intestine as desired to effect topical therapy or to maximize absorption and/or bioavailability of the medicament for systemic therapy.

Yet another object of the present invention is to provide a filament system and method for retarding the passage of the reservoir from which the medicament is released through the intestine, thereby extending the period of time over which therapeutically effective doses of the medicament& are delivered.

It is another object of the present invention to provide a filament system and method by which the reservoir of medicament to be released at a specific location in the intestine is continually replenished by the passage of the filament through the intestine.

It is another object of the present invention to provide a filament system and method in which the reservoir from which the medicament is delivered does not remain in the gastrointestinal tract permanently, but which is nevertheless capable of delivering effective dosage levels of the medicament for extended periods of time.

Other objects, and the advantages, of the present invention will be made clear to those skilled in the art by the following detailed description of a preferred embodiment thereof.

SUMMARY OF THE INVENTION

These objects are achieved by providing a system for delivery of a medicament in the intestine comprising a coiled elongate filament having a medicament contained therein, the composition of the filament and the medicament being selected so as to allow the filament to uncoil and release the medicament in the intestine after ingestion by an animal, and means integral with the filament for retarding the passage of the filament through the intestine after the filament uncoils. In a presently preferred embodiment, the passage retarding means takes the form of a bioadhesive either incorporated in the material comprising the filament or coating a portion of the filament. The system optionally includes a capsule in which the coiled filament is contained for preventing the uncoiling of the filament after ingestion by an animal and until the capsule reaches the intestine. In a presently preferred embodiment, the capsule is comprised of an enteric material.

As noted, the present invention also contemplates a method which provides the benefits listed above. That method of delivering a medicament to the intestine comprises the steps of ingesting a coiled filament having a medicament contained therein to introduce the coiled filament into the intestine and then uncoiling the coiled filament in the intestine. The composition of the filament, and the medicament, are selected so that, as the filament uncoils, the medicament is released therefrom. The method additionally comprises retarding the passage of the uncoiled filament through the intestine to make possible the delivery of the medicament over an extended period of time. The method may optionally include the step of encapsulating the coiled filament with an enteric material which dissolves, decomposes, disperses, or otherwise disintegrates in the intestine to allow the coiled filament contained therein to uncoil. Both the method and the delivery system of the present invention are better understood by reference to the following description of a presently preferred embodiment thereof.

BRIEF DESCRIPTION OF THE DRAWINGS

FIG. 1 is schematic representation of a filament of the type contemplated for use in accordance with the present invention.

FIG. 2 is a schematic representation of the filament of FIG. 1 after that filament has been coiled and encapsulated for ingestion by an animal in accordance with the present invention.

FIG. 3 is a schematic representation of the disintegration of the capsule of FIG. 2 as disintegration would occur in the intestine of the animal which ingested the capsule.

FIG. 4 is a schematic representation of an animal of the type with which the delivery system and method of the present invention may be advantageously utilized which provides, by the various lines extending therefrom to the other figures, a point of reference for discussion of the method of the present invention.

FIG. 5 is a schematic representation of the uncoiled filament of FIG. 2 with reference to the intestine of the animal of FIG. 4.

FIG. 6 is schematic representation (not to scale) of an isolated section of the intestine of the animal of FIG. 4 having the uncoiled filament of FIG. 5 contained therein.

DETAILED DESCRIPTION OF THE PREFERRED EMBODIMENT

Referring to the figures, there is shown a schematic representation of a presently preferred embodiment of a filament system for delivering a medicament to the intestine at reference number 10. As shown in FIG. 2 and indicated by the arrow 12 from FIG. 2 to the mouth 13 of patient 14 shown in FIG. 4, filament 10 is tightly coiled for ingestion by patient 14. After ingestion, the coiled filament 10 passes through the esophagus 16 of patient 14, through the stomach 18, and into the intestine, specifically the small intestine 20. As shown in FIG. 3 and indicated by arrow 22, once filament 10 reaches the small intestine 20, the filament 10 begins to uncoil, at which point the medicament contained in filament 10 is released.

The material comprising filament 10, and the medicament contained in filament 10, are selected so as to allow the filament 10 to uncoil and release the medicament in the intestine after ingestion by patient 14. The material comprising filament 10 may be any one, or a mixture, of many materials known to those skilled in the art into which the medicament is incorporated for release over an extended period of time.

For purposes of convenience, materials which are appropriate for use in connection with the filament of the present invention are categorized as being water insoluble, semipermeable, enteric, or bioerodible depending upon the manner in which the medicament is released from the material in the intestine. For instance, a material having a medicament dispersed therein from which the medicament migrates without decomposition, dispersion, disintegration, or dissolution thereof is considered either water insoluble or semipermeable. Materials through which aqueous solutions penetrate to dissolve the medicament and cause the medicament to be dispersed therefrom are considered semipermeable. Enteric materials are those which do not dissolve, disperse, decompose, or disintegrate in the stomach during the period of time the filament 10 passes through the stomach as defined in column 6, beginning at line 5, of the above-noted and incorporated U.S. Pat. No. 4,627,851. Materials which dissolve, disperse, decompose, or disintegrate in the intestine to release the medicament are considered bioerodible; a more complete explanation of that term appears throughout U.S. Pat. No. 3,901,232 which, having been incorporated herein by the above reference thereto, need not be repeated here. These categories are not mutually exclusive; many materials appropriate for use as the material comprising filament 10 may be both, for instance, bioerodible and semipermeable such as certain polyurethanes which can be formulated in uncrosslinked, partially crosslinked, or highly crosslinked form, or water insoluble and enteric, such as hydroxypropyl methylcellulose phthalate.

Many such materials are natural products such as keratin, salol, triglycerides, fatty acids, latexes and locust bean gum; derivatives of natural products such as modified collagen and formalized or regenerated proteins; cellulose derivatives such as ethyl cellulose and cellulose acetate derivatives, especially cellulose acetate phthalates; or polymers such as polylactic acid, polyvinylpyrolidone, polyvinyl acetates, and polyethylene oxide. In one particularly preferred embodiment, filament 10 is comprised of a material which is pH sensitive, e.g., materials which are stable in an acid environment such as the stomach but which dissolve, disperse, decompose, or otherwise disintegrate at a pH greater than about 5, and therefore may be utilized to achieve the delivery of the medicament to a specific location in the intestine due to the progressively increasing alkalinity of the intestine. For instance, certain polyvinyl acetate phthalates are available which are capable of releasing the medicament at a pH of 4.5-5.0, e.g., in the area of the intestine 20 immediately below the pyloric valve 24 of the stomach 18. A variety of pH sensitive polyacrylic acids are available, for instance those sold under the brand name EUDRAGITS (Rohm-Tech), which are capable of releasing the medicament at a desired pH ranging from about 5.5 (L-100-55) up to as high as 7.0 (S-100). Cellulose acetate trimellitate is also pH sensitive, being capable of releasing the medicament at a pH greater than about 5.5. When it is desired to deliver the medicament to an area even farther down the intestine, a material such as shellac, which begins to dissolve at a pH greater than about 7.4, is utilized. Other pH sensitive materials include hydroxypropyl methyl cellulose phthalate and cellulose acetate phthalate.

Many other water insoluble, semipermeable, enteric or bioerodible materials which are appropriate for use as the material comprising the filament 10 are known to those skilled in the art. They include, but are not limited to, polyethylene, polybutene and certain other polyalkenes; paraffin, natural, and microcrystalline waxes; hydrocarbon resins; mono- and diglycerides; a wide assortment of cellulose derivatives such as cellulose acetyl, diacetyl and triacetyl phthalate, cellulose ester and ether phthalate, methylcellulose phthalate, hydroxypropyl cellulose phthalate, cellulose acetate and hydroxypropyl methylcellulose hexahydroxyphthalate, cellulose acylate, and cellulose di- and triacylate; salts of various cellulose derivatives such as the sodium, calcium, alkali or alkaline earth salt of cellulose acetate phthalate and the ammonium salt of hydroxypropyl methylcellulose phthalate; polymers of acrylic acid and acrylic acid derivatives such as polymethacrylate esters, polyesters of acrylic and methacrylic acid, uncrosslinked hydroxyalkyl acrylates and methacrylates, and other $\alpha,\beta$-ethylenically unsaturated mono- and dicarboxylic acids and/or anhydrides; polyglycolic acid and derivatives of polyethylene glycol; many polymers and co-polymers such as ethylene-vinyl acetate polymer and partial or completely hydrolyzed ethylene-vinyl acetate co-polymers, vinylidene chloride/acrylonitrile polymer, highly plasticized polyvinyl chloride, homo- and co-polymers of polyvinyl acetate, polyvinyl alkyl ethers, polyvinyl fluoride, silicone polycarbonates, silicone elastomers, polymeric epoxides, co-polymers of an alkylene oxide and alkyl glycidyl ether, derivatives of polystyrene such as poly(-sodium styrenesulfonate) and poly(vinyl benzyltrimethyl-ammonium chloride) and the so-called "block" polymers, polyimides, polybenzimidazoles. selectively permeable polymers formed by coprecipitation of a polycation and a polyanion as described in U.S. Pat. Nos. 3,276,589, 3,541,006, 3,541,055, and 3,546,142, poly(anhydride) polymers as described in U.S. Pat. Nos. 2,073,799, 2,668,162, and 2,676,945, and in Chapter 6 of Stille, J. K., Introduction to Polymer Chemistry, New York: John Wiley Publishing (1962), polyesters as described in U.S. Pat. Nos. 2,668,162, 2,676,945, 2,703,316, and 3,297,033 and in 36 Industrial and Engineering Chemistry 223-228 (1964) and 75 Macrmol. Chem. 211-214 (1964), co-polymers of acrylamide and methacrylamide including up to about 40% by weight of a cross-linker such as N-methylene bisacrylamide or N,N-dimethylurea, and polyethyleneimine; and naturally and modified naturally occurring materials such as starch, fatty alcohols, calcium alginate, calcium caseinate, calcium polypectate, cross-linked gelatin of the type having a cross-linker that is reactive with the hydroxyl, carboxyl, or amino groups of the gelatin molecule as described in 5 J. Polymer Science, Part A-1 (1967), 54 J. Polymer Science 321-335 (1961) and 41 Adv. Protein Chem., "Cross Linkage in Protein Chemistry", New York: Academic Press (1961), and the materials and mixtures of materials listed beginning at line 28 of column 6 of U.S. Pat. No. 4,627,851, listed and incorporated by reference above; and proteins and hydrocolloids of animal and plant origin such as elastin, keratin, fibrin, algin, karaya, pectin, carrageenin, chitin, heparin, and locust bean gum.

The term "medicament" as used herein refers to any pharmacological agent which is advantageously delivered in the intestine and which is capable of being dispersed in the matrix of, or otherwise contained in, i.e., is capatible with the material comprising filament 10. The term "contained" is used herein in a generic sense and is intended to describe the physical relationship between the material comprising filament 10 and the medicament in the case of materials into which the medicament is absorbed, materials in which the medicament is impregnated, materials in which the medicament is dispersed in the matrix comprising the material, materials in which the medicament is dissolved, and materials which surround, coat, and/or or encapsulate the medicament. In other words, the term is intended to include any arrangement by which the material is capable of serving as a reservoir for the medicament and still be capable of being shaped into a filament.

Appropriate medicaments for use in connection with the present invention include, but are not limited to, antibiotics, antioxidants, biocides, hormones, steroids, fungicides, nutritional supplements, vitamins, co-factors, anti-inflammatories, decongestants, antivirals, analgesics-antipyretics, anesthetics, anti-cancer and/or anti-tumor agents, immunostimulants, immunodepressants, monoclonal antibodies and/or other immunological agents, muscle relaxants, central nervous system stimulants or depressants, enzymes, detoxicants, antihistamines, and anti-metabolites. The present invention also contemplates the containment of two or more compatible and/or synergistic medicaments in the same filament or in two or more filaments which are twined together before being coiled for ingestion or which are contained in the same capsule 28 as discussed below. The compounding of these medicaments, and their therapeutically effective dosage levels, are matters known to those skilled in the art and, insofar as those matters are not considered part of the present invention, are not addressed in detail here.

Filament 10 is made by any number of methods known in the art for forming materials such as those listed above for containing the medicament. In a presently preferred embodiment, filament 10 is made with a centrifugal extrusion device or by co-extrusion, both processes being known in the art, hence there is no need to describe them further here. Another example of a process appropriate for manufacturing filament 10 is the commercial process, known as an interfacial polymerization process, for making nylon. Production of filament 10 by extrusion processes also makes possible the changing of the amount of medicament contained in the filament 10, e.g., the concentration of the medicament, along the length of the filament, thereby allowing the control of the dosage delivered in the intestine for topical application or to maximize the bioavailability of the medicament. Extrusion methods also enable the containment of a first medicament in one portion of the filament and one Or more additional medicaments, or alternate formulations of the same medicament, in other portions of the filament for the same purpose. Those skilled in the art who have the benefit of this disclosure will also recognize that filament 10 may contain two or more medicaments which are not contained in spatially distinct portions thereof. In other words, two or more compatible medicaments may be distributed throughout the matrix of the material comprising filament 10 in equal concentrations, or even in overlapping, changing concentrations (e.g., a first medicament in increasing concentration from one end of filament 10 to the other and a second medicament in decreasing concentration from the one end to the other). In the event the medicaments not compatible, one or both is encapsulated with an encapsulant which does not alter their release characteristics from filament 10.

As shown in FIGS. 2 and 3, the coiled filament 10 may be contained in a capsule 26 for ingestion by an animal. Capsule 28 is optional depending upon the composition of the filament 10. For instance, if the material comprising filament 10 is a semipermeable or bioerodible material, it is advantageous to encapsulate such a filament to prevent uncoiling, and the release of the medicament therefrom, until the capsule 28, having the filament 10 coiled therein, reaches the intestine. Those skilled in the art who have the benefit of this disclosure will recognize that two or more filaments may be encapsulated in the same capsule 28 and that each filament may be comprised of different materials or contain different medicaments as may be desired.

To accomplish that function, capsule 28 is preferably comprised of an enteric material as defined above or a pH sensitive material which dissolves, disperses, decomposes, or otherwise disintegrates at the more alkaline (as compared to the pH of the stomach) pH of the intestine (note that many pH sensitive materials are included within the definition of "enteric material" set out herein). A commercially available, two-part gelatin capsule is an example of such a material and represents a presently preferred embodiment of an enteric material which is used to advantage in accordance with the present invention. The method by which the capsule 28 is made depends upon the nature of the material comprising the capsule and, like production of filament 10, can be accomplished in accordance with a number of commerically practiced methods. One such method, pan coating, is described beginning at column 10, line 1 of U.S. Pat. No. 4,627,851, already incorporated by reference in its entirety. Other methods are summarized in U.S. Pat. No. 4,578,075, also incorporated herein in its entirety by this specific reference thereto. Because such methods are known to those skilled in the art, no further description of them is necessary here.

Referring now to FIG. 5, there is shown a schematic representation of filament 10 after uncoiling in the intestine, the arrow 30 providing the point of reference to the intestine 20 of the patient 14. Although present while coiled (see FIG. 3), there is clearly visible in FIG. 5 a means integral with filament 10 for retarding the passage of filament 10 through intestine 20. This passage retarding means may take the form of a bioadhesive "head" 32 at one end of filament 10 or is part of the filament 10 itself in the sense that many of the materials listed above as being appropriate for use as the material comprising filament 10 are tacky. In the case of filaments comprised of such materials, once filament 10 is uncoiled in the intestine 20, the filament 10 is at once both the container or delivery system for the medicament and the passage retarding means. In another embodiment, a bioadhesive is coated along the length of filament 10 by spraying or dipping filament 10 in a solution of the bioadhesive and then drying the coated filament before coiling or encapsulating. In describing this latter embodiment, one reason why the capsule 28 is optional for practicing the present invention is made clear: one function of capsule 28 is to prevent filament 10 from uncoiling until the capsule 28, having the filament 10 coiled therein, reaches the intestine 20. In the case of a filament 10 coated with bioadhesive, the filament 10 need only be coiled before drying (or when partially dry), or dried and then moistened slightly with water or other aqueous solution, to form a layer which effectively prevents filament 10 from uncoiling until reaching the intestine 20.

The bioadhesive may be selected from any one of a number of known, synthetic natural-occurring, or modified naturally-occurring substances which exhibit a measure of stickiness, or "tack". By the use of the term "bioadhesive" it is not required that an adhesive be naturally-occurring; instead, that term is intended to refer to an adhesive with which is bio-compatible, e.g., non-toxic and/or inert in the intended application. The adhesive must also be compatible with the material comprising filament 10 as well as the medicament contained therein. Substances appropriate for use as a bioadhesive in connection with the present invention include, but are not limited to, calcium polycarbophil, polymers of acrylic acid and its derivatives, gelatin, carboxymethyl and hydroxypropyl methyl cellulose, and other cellulose derivatives, karaya, tragacanth, locust bean and other synthetic and naturally occurring gums, algin, chitosan (the presently preferred bioadhesive), starches, pectins, and naturally-occurring resins such as balsam, mastic, and sandarac. Various mixtures of these substances may also be utilized to advantage.

As shown schematically in FIG. 6, the passage retarding means, in the form of head 32, functions by adhering to the intestinal musosa, the remainder, or "tail", of the uncoiled filament 10 extending down intestine 20. A portion of the intestine 20 is shown in FIG. 6, with the arrow 34 providing a point of reference to the patient 14 shown in FIG. 4, and that figure provides an illustration of how filament 10 is utilized to deliver a medicament to a specific location in the intestine 20. As noted above, the pH of the contents of the small intestine becomes increasingly more alkaline as the contents move through the intestine, e.g., in the direction of arrow 36, and as shown schematically in FIG. 6. When filament 10 is comprised of a pH-sensitive material such as the cellulose acetate trimellitate available from Eastman-Kodak or the polyacrylic acids available from Rohm-Tech under the brand name "Eudragits" (catalog/stock no. L-100-55), the medicament contained therein is released in the portion of the intestine 20 in which the pH is greater than about 5.5. The portion of filament 10 having the head 32 integral therewith initially adheres to the intestinal mucosa in an area of the intestine in which the pH is less than 5.5 to retard the passage of filament 10 through the intestine. In this manner, the period of time during which the medicament is delivered to the patient 14, or to the specific portion of the intestine 20 in which the pH is greater than 5.5, is extended because the reservoir of available medicament is continually replenished as the head 32 retards the passage of filament 10 through the portion of intestine 20 in which the pH is less than 5.5. Filament 10 also functions to deliver larger total dosages of the medicament than can be achieved using previously known systems, if desired, because the passage retarding means retains the filament in the intestine for long periods of time.

Dosage levels and the location to which the medicament is to be delivered are control ed by manipulating such parameters as the amount of medicament contained within filament 10 (e.g., the size of the reservoir), the length of filament 10, the permeablility or bioerodibility of the material comprising filament 10, and the pH sensitivity of that material. Additional control is achieved by use of a capsule 28 and the nature of the substance comprising that capsule. For instance, if it is desired to deliver a medicament effective against ulcerative lesions located immediately below the pyloric valve 24 of patient 14, and high local dosage levels are indicated, the filament is formulated from a material into which high concentrations of that medicament can be dispersed and which releases the medicament at a pH just slightly more alkaline than that of the stomach contents, and the filament is made fairly short, e.g., a few inches in length. If low, relatively constant levels of a medicament over long periods of time are desired and that medicament is poorly absorbed at acidic pH, or hydrolyzed or denatured in acid, filament 10 is comprised of a semipermeable material having a relatively low concentration of the medicament dispersed therein and is several feet in length. The long filament is ingested in a capsule comprised of a pH sensitive substance which disperses, disintegrates, decomposes, or dissolves at a pH of, for instance, 6.8 so that the coiled, encapsulated filament does not even begin to uncoil until the capsule is well down the intestine. Once uncoiled, the long length of the filament provides a reservoir large enough to contain a fairly large total amount of the medicament so that the filament can be expected to contain enough medicament to maintain effective dosage levels for a long time, but the relatively low concentration of the medicament in the filament decreases the absorption rate therefrom to maintain the desired low dosage levels. The permeability of the filament can be changed, for instance by using a more highly cross-linked polymer, to provide an even greater degree of control over dosage levels.

Although described in terms of the above presently preferred embodiments of the invention, those skilled in the art who have the benefit of this disclosure will recognize that certain changes can be made to the specific structure thereof without departing from the manner in which that structure functions to achieve the desired results. Such changes are included within the spirit of the invention and are intended to fall within the scope of the following claims.

What is claimed is:

1. A system for delivery of a medicament to the intestine comprising a coiled elongate filament having a medicament contained in the filament, the composition of said filament and said medicament being selected so as to allow said filament to uncoil for releasing said medicament from the uncoiled length thereof in the intestine after ingestion of said coiled filament by an animal, and a bioadhesive integral with said filament for retarding the passage of said filament through the intestine after said filament uncoils by adhering said uncoiled filament to the intestinal mucosa.

2. The delivery system of claim 1 wherein said filament is comprised of a water insoluble, semipermeable, enteric, or bioerodible material having said medicament dispersed in the matrix thereof.

3. The delivery system of claim 1 additionally comprising a capsule in which said coiled filament is contained for preventing the uncoiling of said filament until said capsule, having said coiled filament contained therein, reaches the intestine.

4. The delivery system of claim 3 wherein said capsule is comprised of an enteric material.

5. The delivery system of claim 1 wherein said filament is comprised of a bioerodible material having said medicament dispersed in the matrix thereof.

6. The delivery system of claim 5 additionally comprising a capsule formed of an enteric material in which said bioerodible filament is contained and which releases said coiled, bioerodible filament in the intestine.

7. The delivery system of claim 1 wherein said bioadhesive is selected from the group consisting of calcium polycarbophil, gelatin, polymers of acrylic acid and derivatives thereof, carboxymethyl and hydroxypropyl methyl cellulose and other cellulose derivatives, natural and synthetic gums, algin, chitosan, starches, pectins, and naturally-occurring resins, and mixutres thereof.

8. A device for delivery of a medicament in the intestine comprising:
    a coiled filament;
    a medicament contained within said filament, said medicament and the composition of said filament being selected so that said medicament is released from said filament after said filament uncoils after being introduced into the intestine;
    a bioadhesive integral with said filament for adhering said filament to the intestinal mucosa after said filament uncoils in the intestine to retard the passage of said uncoiled filament through the intestine; and
    a capsule in which said filament is contained for preventing the uncoiling of said filament, and the release of said medicament therefrom, until said capsule is introduced into the intestine.

9. The device of claim 8 wherein said filament is comprised of a water insoluble, semipermeable, enteric, or bioerodible material having said medicament dispersed in the matrix thereof.

10. The device of claim 8 wherein said capsule is comprised of an enteric material.

11. The device of claim 8 additionally comprising means for retarding the passage of said filament through the intestine after said filament uncoils.

12. A method of delivering a medicament to the intestine comprising the steps of:
    ingesting a coiled filament having a medicament contained therein to introduce the coiled filament into the intestine;
    uncoiling the coiled filament in the intestine, the material comprising the coiled filament and the medicament being selected so that, as the filament uncoils to expose the length of the filament to conditions in the intestine, the medicament is released therefrom; and retarding the passage of the uncoiled filament through the intestine, thereby causing the medicament to be released in the intestine over an extended period of time.

13. The method of claim 12 additionally comprising preventing the uncoiling of the filament until the filament reaches the intestine.

14. The method of claim 12 additionally comprising encapsulating the coiled filament in an enteric material to prevent the uncoiling of the filament until the capsule reaches the intestine.

15. The method of claim 12 wherein the medicament is released from the filament at a specific location in the intestine, the material comprising the filament being selected so as to release the medicament therefrom when exposed to a selected pH, the selected pH corresponding to the pH of the specific location in the intestine at which it is desired to release the medicament.

16. The method of claim 15 wherein the reservoir of medicament to be released at the specific location in the intestine is continually replenished by the retarded passage of the uncoiled filament through the intestine.

17. The method of claim 12 wherein passage of the uncoiled filament is retarded by adhering the uncoiled filament to the wall of the intestine.

18. A filament system for delivery of a medicament comprising:

a coiled elongate filament comprised of a material selected from the group consisting of water insoluble, semipermeable, enteric, or bioerodible materials and having a medicament dispersed in the matrix thereof;

a capsule in which said filament is contained until said capsule is introduced into the intestine of an animal, said capsule being comprised of an enteric material; and said filament additionally comprising a bioadhesive for retarding the passage of said filament through the intestine after said filament uncoils in the intestine.

19. The delivery system of claim 5 wherein the bioerodible material comprising said filament is sensitive to a pH found at a specific location in the intestine.

* * * * *